United States Patent [19]

Hardy

[11] 4,092,113

[45] May 30, 1978

[54] PREPARATION OF BLOOD PLASMA AND SERUM SAMPLES

[75] Inventor: Stanley Matthias Hardy, Huntingdon, England

[73] Assignee: Aesculapius Scientific Limited, England

[21] Appl. No.: 724,064

[22] Filed: Sep. 16, 1976

[30] Foreign Application Priority Data

Sep. 24, 1975 United Kingdom ............... 39075/75
Aug. 23, 1976 United Kingdom ............... 34957/76

[51] Int. Cl.$^2$ ........................................... G01N 33/16
[52] U.S. Cl. .................................... 23/230 B; 23/259; 210/DIG. 23; 210/DIG. 24; 233/1 R
[58] Field of Search ............................. 23/230 B, 259; 210/DIG. 23, DIG. 24

[56] References Cited

U.S. PATENT DOCUMENTS

| | | | |
|---|---|---|---|
| 3,800,947 | 4/1974 | Smith | 210/DIG. 23 X |
| 3,807,955 | 4/1974 | Note, Jr. | 210/DIG. 23 X |
| 3,954,614 | 5/1976 | Wright | 210/DIG. 23 X |
| 3,960,727 | 6/1976 | Hochstrasser | 210/DIG. 23 X |
| 3,972,812 | 8/1976 | Gresl, Jr. | 210/DIG. 23 X |

*Primary Examiner*—Sidney Marantz
*Attorney, Agent, or Firm*—Browdy and Neimark

[57] ABSTRACT

In a method of preparing a plasma sample, blood from a donor is placed in the inner of two concentric tubes which are releasably connected together. The outer sample tube is labelled with data relating to the blood sample. After the concentric sample tubes have been centrifuged to separate out plasma from the blood, the outer tube is disconnected from the inner tube so that plasma can be poured into the outer tube. The outer tube, which carries the label, is then retained for analysis. As an alternative to centrifuging, a leakage path which is permeable to plasma but not blood cells can be provided at the base of the inner tube and plasma forced into the outer tube by application of external pressure.

31 Claims, 5 Drawing Figures

PREPARATION OF BLOOD PLASMA AND SERUM SAMPLES

BACKGROUND OF THE INVENTION

This invention relates to the preparation of samples of blood plasma and blood serum for analysis. It will be appreciated that if blood cells are separated from a whole blood sample the supernatent will comprise plasma if a suitable anticoagulant is present or serum if clotting is allowed to occur. This invention is equally applicable to samples of plasma or serum though for convenience the invention is described throughout in terms of blood plasma samples.

In a typical hospital procedure, a sample of blood is taken from a donor patient on the ward and is placed in a blood sample tube. The tube is then sealed and labelled with the name of the donor, the date and time and any such other data relevant to the identity of the blood sample that is required. The sealed sample tube is transported to the laboratory where a technician copies the information on the sample tube label to an empty plasma sample tube. The blood sample tube is then centrifuged to separate the plasma constituent of the blood from the blood cells and the plasma transferred to the labelled plasma sample tube either by pipette or simply by pouring if an amount of special plastic beads has been added to the blood sample prior to centrifuging so that on centrifuging a barrier is formed between the plasma and the blood cells. Both sample tubes are then sealed with screw caps, the blood sample tube being discarded to avoid contamination and the labelled plasma tube retained for subsequent analysis.

This procedure involves certain steps at which errors may occasionally occur unless the technician exercises extreme care. Thus, for example, the technician is required to copy the data from the blood sample tube onto the label for the plasma sample tube; almost inevitably mistakes will be made from time to time. In addition, the normal procedure invites the technician to label a batch of, say, sixteen plasma sample tubes with data corresponding respectively with sixteen blood sample tubes which have been sent from the ward. After centrifuging, the plasma from each blood sample tube has to be transferred to the appropriate plasma sample tube; the risk of plasma being transferred into a wrongly labelled sample tube is self evident.

SUMMARY OF THE INVENTION

It is an object of this invention to provide an improved method of preparing a sample of blood plasma which reduce the opportunities for errors that result in the plasma sample being incorrectly labelled.

Accordingly, the present invention consists in a method of preparing a labelled sample of blood plasma or serum comprising the steps of taking a sample of blood from a donor, placing the sample of blood in the inner of two sample vessels which are releasably connected together one inside the other; labelling the outer of the two vessels with data relevant to the identity of the blood sample; separating and conveying plasma or serum constituent of the blood sample from the inner to the outer of the two vessels; and retaining the labelled outer vessel containing the plasma or serum for subsequent analysis.

In one form of the invention the step of separating and conveying plasma or serum constituent of the blood sample from the inner to the outer of the two vessels comprises the steps of centrifuging the two sample vessels releasably connected together one inside the other to separate plasma or serum constituent of the blood sample; disconnecting the outer from the inner of the two sample vessels; and transferring plasma or serum constituent of the blood sample from the inner to the outer of two sample vessels;

In another form of the invention the step of placing the sample of blood in the inner of two sample vessels which are releasably connected together one inside the other, comprises the step of placing the sample of blood in the inner sample vessel which includes a leakage path communicating between the two vessels permeable to blood plasma but not to blood cells; and the step of separating and conveying plasma or serum constituent of the blood sample from the inner to the outer of the two vessels comprises the step of applying a pressure difference across said leakage path to the force plasma or serum constituent of the blood sample from the inner to the outer of the two vessels.

BRIEF DESCRIPTION OF THE DRAWINGS

The invention will now be described by way of example with reference to the accompanying drawings in which.

DESCRIPTION OF THE PREFERRED EMBODIMENT

Figure 1:
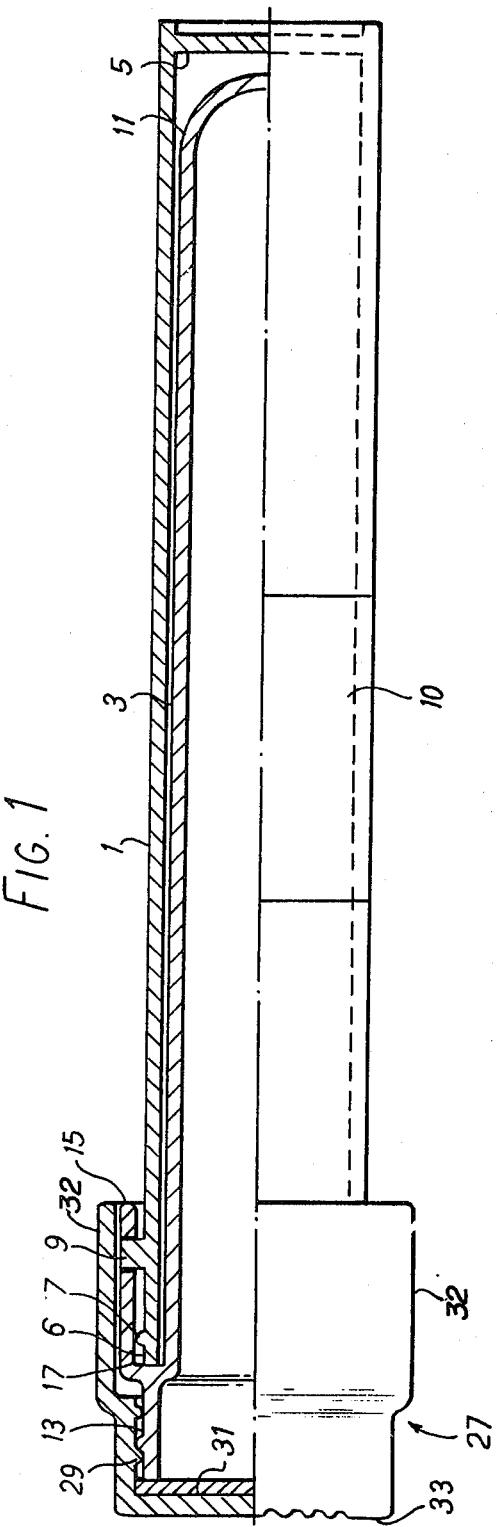
FIG. 1 is a front elevation, partly in section, of a device according to the invention.
Figure 3:
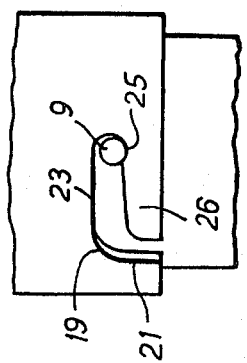
FIG. 3 is a detail in rear elevation of FIG. 2 with one part of the device removed.
Figure 2:
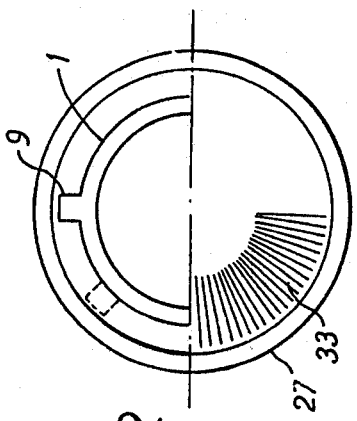
FIG. 2 is an end elevation and section of FIG. 1.

The device shown in FIGS. 1, 2 and 3 comprises an outer plasma sample tube 1 and an inner blood sample tube 3 both injection moulded, for example, in polystyrene. The outer tube is cylindrical and is closed at one end by a disc 5. At the other end 6 it is provided with a screw thread 7 for co-operation with a conventional screw cap (not shown), and a pair of radially projecting and diametrically opposed studs 9. A labelling area 10 is provided on the outside of the outer tube with appropriately marked sections for the data specified in BS 4851. This labelling area may be formed by suitably treating the surface of the tube to enable a label to be written in ink or may comprise a sheet of paper suitably adhered to the surface of the tube. The inner tube 3 is positioned coaxially within the outer tube and has a rounded, closed end 11. Remotely from this closed end the inner tube is provided with a screw threaded rim 13 and an integral, annular sleeve 15 which extends coaxially of the inner tube toward the closed end 11. The open end 6 of the outer tube is received within the recess formed between the cylindrical portion of the inner tube and the sleeve 15, and in fact contacts the inner tube at the shoulder 17 at the base of this recess.

The inner and outer tubes of the device are connected together with a bayonet fitting which comprises studs 9 of the outer tube and corresponding L-shaped slots 19 formed in the sleeve 15 of the inner tube. As best seen in FIG. 3, each slot 19 has a short portion 21 which extends axially of the tubes and which communicates with a longer, angularly extending portion 23. The assembly of the two tubes is effected by an initial axial displacement of the outer tube, during which each stud travels along the portion 21 of the corresponding slot, followed by a relative rotation of the tubes with the studs moving along the slot portions 23. The closed end of each slot is formed with an enlargement 25 which co-operates with the corresponding stud 9 to provide a snap engagement at the end of the relative rotational movement. This bayonet type fitting thus provides a releasable connection between the two tubes.

In an advantageous modification, the enlargement 25 is made more pronounced with the assembly of the tubes being carried out at an increased temperature so that tongue 26 of the sleeve 15 can flex without fracture to permit the entry of the pin 9 into the enlargement 25. If an attempt is made to disconnect the tubes at normal temperatures, however, relative rotation between the tubes will cause pin 9 to fracture tongue 26.

The device is provided with a cap 27 internally threaded at 29 to co-operate with the screw threaded rim 13 of the inner tube. In an advantageous modification, the screw thread of the rim 13 is sufficiently different from the screw thread 7 of the outer tube for it to be difficult for the cap 27 to be screwed on to the outer tube 1. This can be achieved in various ways such as having one thread double start and the other single start. The advantages of this modification will be made clear later in this description. A disc seal 31 is positioned within the cap to ensure a liquid tight closure of the inner tube whilst the periphery of the cap is knurled at 33 to assist in tightening and loosening of the cap. For a purpose that will become apparent, the screw thread 29 is arranged so that the torque required to loosen the cap 27 is less than that required to overcome the snap engagement of the studs 9 with the enlargements 25 provided at the ends of the slots of the bayonet fitting. The cap is further provided with an annular skirt 32 which projects over the sleeve 15 of the inner tube.

The method of preparing a blood plasma sample according to the present invention can now be understood. The nurse or other person taking the blood sample will be provided with a device as assembled in FIG. 1 with the inner sample tube containing a small quantity of polystyrene beads whose function will be described hereinafter, together with any such additives, for example an anti-coagulant, as are necessitated by the particular analysis to be undertaken. If the device has been modified as described above so that tongues 26 fracture at disconnection of the tubes, the nurse will be instructed to check the bayonet fitting to determine whether the device has been used before. If the tongues are broken, the device should be discarded. The outer sample tube 1 is then labelled with the necessary data relevant to the identity of the blood sample. This data will usually include the name and date of birth of the patient, the reference number and ward and the date and time of taking the sample, though other information will be required for certain analyses. The cap 27 is then unscrewed and a sample of blood taken from the donor patient by conventional means and placed in the inner sample tube 3, the cap is then screwed back on to the device. During this sequence, the inner and outer tubes will remain connected together unless the nurse makes a conscious effort to depart from the normal procedure. Two features of the device combine to discourage the nurse from separating the two sample tubes. First, as described above the torque required to separate the cap 27 from the inner tube 3 is less than the torque required to separate the outer tube 1 from the inner tube. In consequence, a turning movement of the cap 27 with the outer tube held, will result in unscrewing of the cap in preference to unlocking of the bayonet fitting between the two tubes. Second, since the skirt 32 of the cap completely covers the sleeve 15 of the inner tube, in the assembled device no part of the inner tube is exposed.

The device containing the blood sample and labelled with the relevant information can now be transported to the laboratory. It will be appreciated that at this time the blood sample is enclosed within a "double-walled" container so that the risk of contamination by the blood sample upon accidental breakage of the sample tube is substantially reduced. This is important where, for example, the device is sent by post to the laboratory, since breakage of the outer sample tube will not, as would be the case with conventional sample tubes, lead to spillage of the blood sample. This reduction in the likelihood of the blood sample leaking from the tube is important even in hospitals where the samples need be transported only a short distance to the laboratory, since on those occasions a blood sample may contain viruses associated with infectious diseases and any reduction in the chances of contamination upon fracture of a sample tube is well worthwhile achieving.

Figure 4:
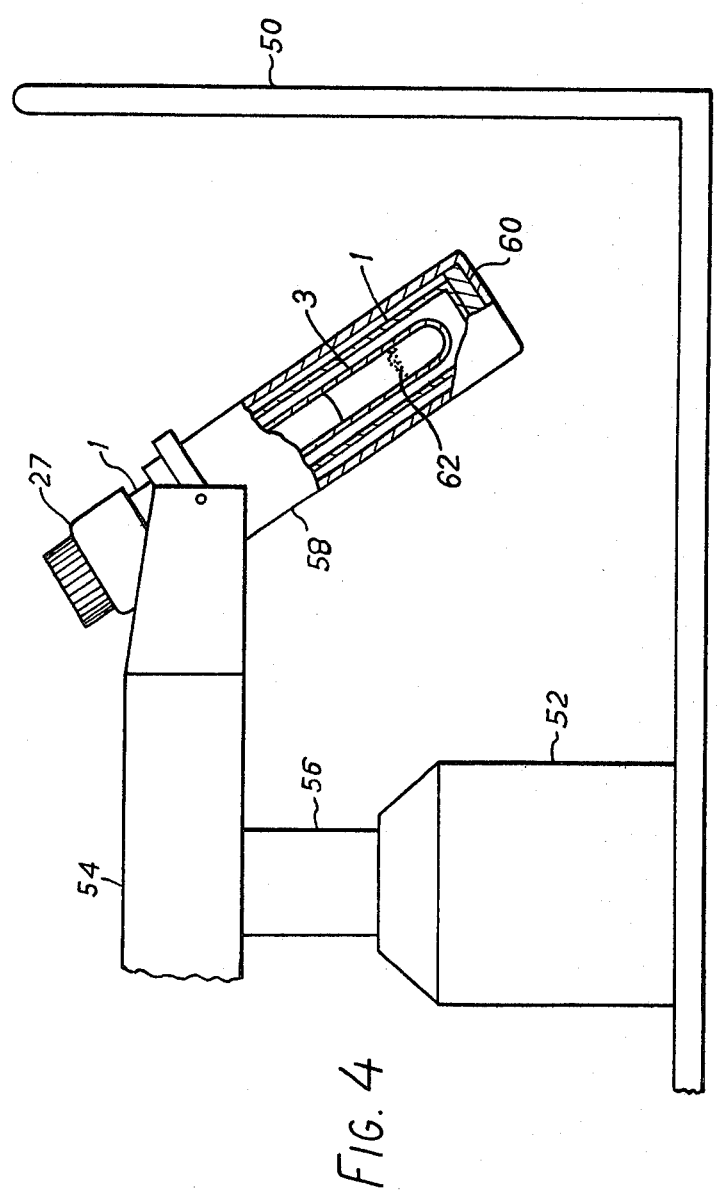
FIG. 4 illustrates diagrammatically one step of the method according to the invention.

In the laboratory, the technician places the whole device in the bucket of a conventional centrifuge as illustrated in FIG. 4, and it will be noted that the cylindrical shape of the outer tube allows the device to be positioned correctly in the bucket. The centrifuge comprises a housing 50 and a motor 52 secured to the housing for rotating a head 54 mounted on a shaft 56. A bucket 58 is pivotally mounted to the head so as to be able to "swing out" toward the horizontal position upon rotation of the head. A typical centrifuge has around sixteen buckets although only one is shown in the drawing for clarity. The device containing the blood sample is positioned in the bucket 58 and rests on a cushion 60 provided at the bottom of that bucket. It should be noted that the sample tubes are sufficiently long for the cap 27 to be clear of the top edge of the bucket so that outward movement of the device is resisted solely by the cushion 60. The overall length of the device must be such, however, that swinging out of the bucket is permitted without the cap 27 fouling the head of the centrifuge. It should also be noted that since the open end of the outer sample tube (see FIG. 1) contacts the inner tube at the shoulder 17, outward movement of the inner sample tube is resisted by the outer tube in compression and no force is transmitted by the bayonet fitting. In some cases this function could alternatively be performed by one or more radial projections from the inner tube.

Centrifuging of the blood sample causes the plasma constituent to separate out, with the more massive blood cells moving to the base of the inner sample tube. The polystyrene beads 62 will adopt a position intermediate the plasma and the blood cells, forming a crust. The risk of breakage during the centrifuging leading to spillage of the blood sample is again, minimized by the double walled nature of the device. At the end of the prescribed period, which will of course depend upon the speed of rotation of the centrifuge, the device is removed. The cap 27 is unscrewed from the rim 13 of the inner tube and put to one side. The technician then twists the inner tube 3 — which can be gripped at the sleeve 15 — relatively to the outer tube and withdraws the inner tube axially. The plasma is poured into the outer sample vessel with the crust of polystyrene beads holding back the blood cells. The original cap 26 is screwed onto the inner tube 3 which may then be discarded. A fresh, standard screw cap is used to seal the outer vessel which contains the plasma ready for analysis and on its outer surface, all the relevant data relating to the identity of the blood sample. With the advantageous modification described earlier, it is very difficult for the technician to screw the original — possibly contaminated — screw cap 26 onto the outer plasma vessel. The correct procedure of using a fresh cap to seal the plasma vessel is therefore encouraged.

The advantages of this method are many. First, for example, the previously required label copying operation is eliminated, since the sample tube which will ultimately contain the plasma sample is labelled in the ward as the outer sample tube of the device. Time is thus saved but, more importantly, an opportunity for error on the part of the technician is removed. Second, the likelihood of plasma being transferred into the wrong plasma sample tube is greatly reduced. It will be appreciated that once the two tubes have been separated after centrifuging, the natural step is immediately to pour the plasma from the inner to the outer sample tubes. As a further safeguard, the rounded end 11 of the inner sample tube 3 prevents that tube from being placed upright on a bench, so that the technician is discouraged from putting down the two sample tubes once separated, until he has poured off the plasma and resealed the inner sample tube. Even if the technician is handling 16 blood samples in one batch, only one device can be dealt with at a time, unless the technician takes quite deliberate steps to circumvent the normal procedure, and the chance of the plasma being transferred to the wrong outer sample tube is minimal.

The described technique of using polystyrene beads to form a barrier between the blood cells and the plasma on centrifuging is advantageous, since it permits straightforward pouring of the plasma from the inner to the outer of the two sample tubes. It is not, however, essential to this form of the present invention since the separated plasma could be conveyed to the outer tube by other means — a pipette for example. The described form of centrifuge should, furthermore, be taken as only one method of performing the necessary separation. There are, for example, a great variety of centrifuges in use, most of which will be quite suitable. In any event the separation of plasma in a blood sample is a well understood operation and the persons skilled in the art will be aware of the techniques available to them.

Figure 5:
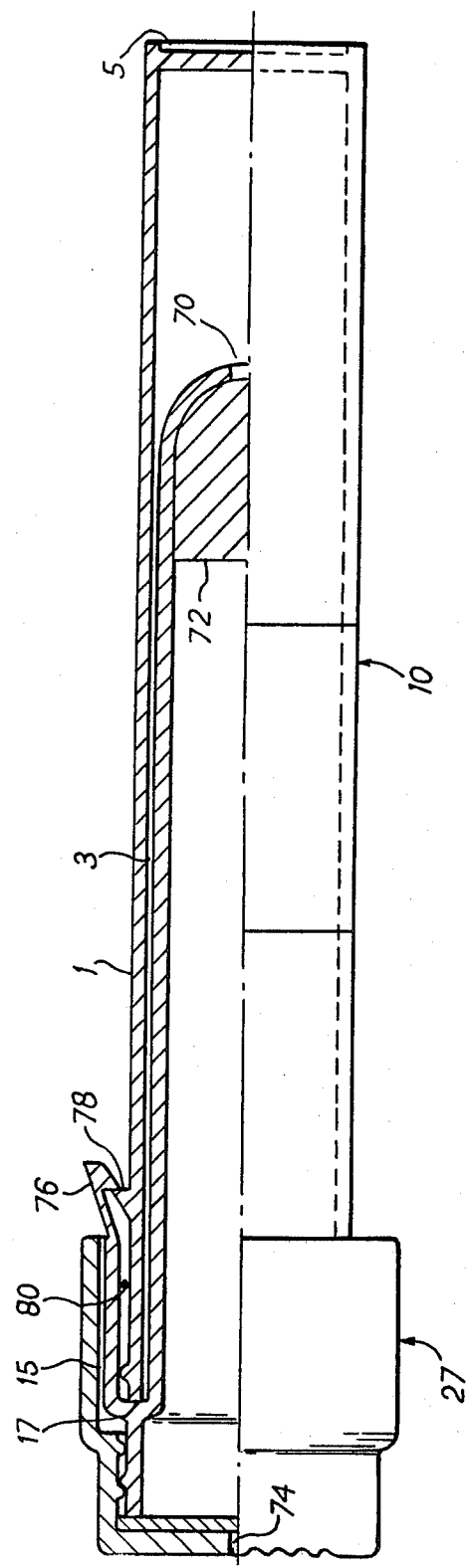
FIG. 5 is a front elevation of a further embodiment of the invention.

A further embodiment of the present invention is illustrated in FIGS. 5 and 6 which show a device which is similar in many respects to that previously described. It will, accordingly, only be described in detail insofar as it differs from the embodiment of FIGS. 1, 2 and 3.

The inner sample tube 3 is provided at its rounded end 11 with an aperture 70 which is covered by a filter 72. This filter is formed of material chosen to have a pore size typically 3 - 5 microns that permits the passage of blood plasma but not of blood cells. The cap 27 of the device has a small axial hole 74 that is normally closed by seal 31. The releasable connection between the two tubes is in this embodiment effected by means of three toothed pawls 76 formed integrally with sleeve 15 and equispaced around the periphery of that sleeve. Each pawl 76 co-operates with a complementarily shaped notch 78 which is formed integrally with the outer tube. An O-ring 80 between the outer tube 1 and the sleeve 15 serves to form a seal. The device is assembled by simply pushing the two tubes together, with each pawl 76 flexing outwards to clear the corresponding notch and then snapping backwards under its own resilience. The method of placing the blood sample in the device at the ward is as described hereinbefore. In the laboratory, however, a centrifuge is not required. Instead, an inert gas is injected into the inner sample vessel by means of a hollow needle pushed through the hole 74 in the cap thus puncturing the seal 31. The increased pressure above the blood sample in the inner tube will force only the blood plasma through the leakage paths formed by the filter 72 and aperture 70 into the outer sample tube. The outer sample tube containing the plasma is then separated from the inner tube by a twisting action which snaps off each of the pawls 76, and is then capped. If desired the procedure can be arranged so that residual pressure in the outer tube forces the outer tube away from the inner tube once the pawls 76 are broken. It may also be advantageous in certain circumstances to arrange matters so that the outer tube can easily be removed from the inner tube without prior removal of the cap, so that once the blood sample has been placed in the inner sample tube, the cap need never be removed.

Since separation of the two tubes causes fracture of each of the pawls, it will again be difficult for the device to be knowingly reused. The desirable practice of disposing of each sample tube immediately after use is therefore encouraged. In a modification, the pawls could be arranged to deform permanently to permit separation of the tubes. This permanent deformation would then serve as an indication that the tubes had been used before.

It will be appreciated that in the embodiment the steps of separating the plasma and conveying the plasma from the inner to the outer of the sample tubes, are in fact accomplished in one step by forcing the plasma through an aperture covered by a filter impermeable to blood cells.

It should be understood that this invention has been described by way of example only and numerous modifications could be made to the methods and devices described herein without departing from the scope of the present invention. For example, the step of taking a blood sample could be accomplished with the known vacuum guns using previously evacuated sample tubes. In this case the inner sample tube 3 would be evacuated. The labelling of the outer sample tube could be effected after the blood sample has been placed in the inner sample tube and the label could comprise an adhesive label placed on a suitable area of the outer sample tube. The devices could be provided with means other than the described bayonet fitting for releasably connecting together the two sample vessels. The two vessels for example be welded together via a thin spigot, with the spigot being broken upon twisting of the tubes. This type of irreversible connection has the advantage that reuse of the sample tube is discouraged. The shape and configuration of the device could be changed considerably from that described with, for example, the cap being secured to the outer rather than the inner tube or the releasable connection between the two tubes being effected remotely from the cap or the closed end of the inner tube being conically shaped rather than rounded. A further modification would involve separation and conveying of plasma through filter 72, instead of using pressure, by suction applied by means of partly with-drawing the outer from the inner tube. With this technique the O-ring 80 is disposed not as shown in FIG. 5 but instead between the outer wall of inner tube 3 and the inner wall of outer tube 1, so that a seal is maintained during initial axial separation of the tubes. Alternatively, the end of the inner tube adjacent the filter could be outwardly flared to provide a circumferential projection which engages the inner cylindrical surface of the outer tube.

What we claim is:

1. A method of preparing a labelled sample of blood plasma or blood serum comprising the steps of taking a sample of blood from a donor; placing the sample of blood in the inner of two sample vessels which are releasably connected together one inside the other; labelling the outer of the two vessels with data relevant to the identity of the blood sample; separating and conveying plasma constituent of the blood sample from the inner to the outer of the two vessels; and retaining the labelled outer vessel containing the plasma for subsequent analysis.

2. A method according to claim 1 comprising the further step prior to disconnection of the two vessels of checking indicator means actuable on disconnection of the vessels, to determine whether the vessels have been used before.

3. A method according to claim 1, wherein in the step of placing the sample of blood in the inner of two sample vessels, the sample is placed in a generally cylindrical sample tube having a closed end which is sufficiently outwardly convex for the sample tube to be unstable if balanced on that end.

4. A method according to claim 1, wherein in the step of placing the sample of blood in the inner of two sample vessels, the sample is placed in the inner of two concentric sample tubes connected together by means releasable upon relative rotation of the two tubes, the tubes having a screw threaded cap adapted to seal the inner sample tube and so arranged that removal of the cap requires less torque than the torque required to separate the two sample tubes.

5. A method according to claim 1, wherein in the step of labelling the outer of the two vessels, data relevant to the identity of the blood sample is written upon an area of the external surface of the outer vessel which has been treated to receive ink.

6. A method according to claim 1, wherein in the step of placing the sample of blood in the inner of two sample vessels, the sample is placed in the inner of two sample vessels which are formed of translucent plastics material.

7. A method according to claim 1 wherein the step of separating and conveying plasma constituent of the blood sample from the inner to the outer of the two vessels comprises the steps of centrifuging the two sample vessels releasably connected together one inside the other to separate plasma constituent of the blood sample; disconnecting the outer from the inner of the two sample vessels; and transferring plasma constituent of the blood sample from the inner to the outer of the two sample vessels.

8. A method according to claim 7 further comprising the step of placing a quantity of plastics beads in the inner vessel before said separating and conveying step, the plastics beads being adapted upon subsequent centrifuging to form a barrier between the plasma or serum constituent of the blood sample; and wherein the step of transferring plasma or serum constituent of the blood sample comprises the step of pouring plasma or serum from the inner to the outer of the two vessels.

9. A method according to claim 1, wherein in the step of placing the sample of blood in the inner of two sample vessels, the sample is placed in the inner of two sample vessels which are releasably connected together by means of a bayonet fitting having pins projecting radially from one of the sample vessels for cooperation with respective slots formed in the other one of the sample vessels.

10. A method according to claim 9, wherein the slots of the bayonet fitting are adapted to provide a snap engagement between the two vessels.

11. A method according to claim 1, wherein in the step of placing the sample of blood in the inner of two sample vessels, the sample is placed in the inner of two vessels releasably connected together by means of a pawl resiliently connected to one vessel and cooperable with notch means formed on the other vessel.

12. A method according to claim 11, wherein the pawl is adapted to undergo a permanent deformation or to fracture upon disconnection of the vessels.

13. A method according to claim 1 wherein the step of placing the sample of blood in the inner of two sample vessels which are releasably connected together one inside the other, comprises the step of placing the sample of blood in the inner sample vessel which includes a leakage path communicating between the two vessels permeable to blood plasma but not to blood cells; and the step of separating and conveying plasma or serum constituent of the blood sample from the inner to the outer of the two vessels comprises the step of applying a pressure difference across said leakage path to force plasma or serum constitutuent of the blood sample from the inner to the outer of the two vessels.

14. A method according to claim 13, wherein said leakage path comprises an aperture in the inner vessel covered by a porous filter having a mean pore size between 3 and 5 microns.

15. A method according to claim 13, wherein in the step of applying a pressure difference across said leakage path, inert fluid is injected into the inner vessel through an aperture in a cap sealing the inner vessel.

16. A method according to claim 13, wherein in the step of placing the sample of blood in the inner of two sample vessels, the sample is placed in the inner of two generally cylindrical and concentric sample tubes provided with means for maintaining a seal between the tubes upon an initial axial separation of tubes and wherein the step of applying a pressure difference across said leakage path comprises the step of axially separating the two tubes.

17. A method according to claim 16, wherein said means for maintaining a seal comprises an O-ring positioned between the sample tubes.

18. A method according to claim 1 wherein in the step of placing the sample of blood in the inner of two vessels, the sample of blood is placed in the inner of two generally cylindrical sample tubes, the inner sample tube being positioned in parallelism within the outer sample tube with the opening of the inner tube adjacent the opening of the outer tube.

19. A method according to claim 18, wherein the outer sample tube is provided with means engageable with a cap to effect sealing of the outer tube.

20. A method according to claim 19, wherein the inner sample tube projects through the opening in the outer sample tube and is engageable with a screw threaded cap to effect sealing of the inner tube.

21. A method according to claim 20, wherein the outer tube is provided with screw thread means engageable with a cap, said means being arranged so as not to be engageable with a screw threaded cap engageable with the inner tube.

22. A method according to claim 18, wherein the inner sample tube is provided with an abutment which projects radially outward from the inner tube and which engages the open end of the outer tube.

23. A method according to claim 22, wherein said abutment comprises a circumferentially extending shoulder which serves to seal the opening of the outer tube.

24. A method according to claim 23, wherein the inner sample tube has an external coaxial annular sleeve which is formed integrally with the shoulder and which extends in a direction away from the opening in the inner tube, the open end of the outer tube being located inside the sleeve.

25. A method according to claim 24, comprising the further step subsequent to the step of placing the sample of blood in the inner sample tube, of engaging a screw threaded cap with the inner sample tube to seal the opening therein, the cap having an annular skirt adapted to cover the sleeve of the inner sample tube.

26. A device for use in the preparation of a labelled blood plasma or serum sample, comprising an inner blood sample vessel adapted to receive a sample of blood and contained within an outer plasma or serum sample vessel which is provided with an area adapted to enable labelling and which is adapted to receive a sample of blood plasma or serum derived from blood contained within the inner blood sample vessel; and means for releasably connecting together the two vessels; the two sample vessels each comprising a generally cylindrical sample tube having an opening at one end thereof, the inner sample tube being positioned in parallelism within the outer sample tube with the opening of the inner tube adjacent the opening of the outer tube, and wherein the inner sample vessel has a leakage path communicating between the two vessels permeable to blood plasma and blood serum but not to blood 27. A device as claimed in claim 26, wherein the leakage path comprises an aperture in the inner vessel covered by a porous filter having a mean pore size between 3 and 5 microns.

28. A device as claimed in claim 26, wherein the inner vessel is provided with a cap having a sealable aperture through which fluid may be injected into the inner vessel.

29. A device as claimed in claim 26 wherein the device further comprising means for maintaining a seal between the inner and outer tubes during an initial axial separation of the tubes.

30. A device as claimed in claim 29 wherein said means for maintaining a seal comprise an O-ring positioned between the sample tubes.

31. A device as claimed in claim 29 wherein said means for sealing comprise a circumferentially extending radial projection formed integrally with the inner tube at a location spaced from the opening thereof and engaging the inner cylindrical surface of the outer tube.

* * * * *